(12) United States Patent
Ieda

(10) Patent No.: US 8,345,397 B2
(45) Date of Patent: Jan. 1, 2013

(54) SENSOR CONTROL APPARATUS AND SENSOR CONTROL METHOD

(75) Inventor: Norikazu Ieda, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 158 days.

(21) Appl. No.: 13/026,696

(22) Filed: Feb. 14, 2011

(65) Prior Publication Data

US 2011/0199709 A1    Aug. 18, 2011

(30) Foreign Application Priority Data

Feb. 15, 2010 (JP) ................................. 2010-029635

(51) Int. Cl.
*H02H 3/08* (2006.01)
(52) U.S. Cl. ...................................................... 361/93.1
(58) Field of Classification Search .................... None
See application file for complete search history.

(56) References Cited

U.S. PATENT DOCUMENTS

| | | | | |
|---|---|---|---|---|
| 4,664,886 A | * | 5/1987 | Novack et al. | 422/94 |
| 5,719,778 A | * | 2/1998 | Suzumura et al. | 700/207 |
| 7,142,976 B2 | | 11/2006 | Inoue et al. | |
| 7,681,560 B2 | * | 3/2010 | Yamaoka et al. | 123/568.11 |
| 7,713,391 B2 | | 5/2010 | Inoue et al. | |
| 2005/0288847 A1 | | 12/2005 | Inoue et al. | |
| 2006/0157348 A1 | | 7/2006 | Inoue et al. | |
| 2008/0060941 A1 | | 3/2008 | Ieda et al. | |

FOREIGN PATENT DOCUMENTS

| | | |
|---|---|---|
| JP | 2004127037 A | 4/2004 |
| JP | 2005-083896 A | 3/2005 |
| JP | 3833687 B2 | 2/2006 |
| JP | 2006047278 A | 2/2006 |
| JP | 2006208363 A | 8/2006 |
| JP | 2008-070194 A | 3/2008 |

* cited by examiner

*Primary Examiner* — Stephen W Jackson
*Assistant Examiner* — Terrence Willoughby
(74) *Attorney, Agent, or Firm* — Sughrue Mion, PLLC

(57) ABSTRACT

A sensor control apparatus (100) includes a signal output section (60) which outputs an instruction signal for selecting a drive or protection mode, and a drive circuit (70) which controls the supply of electric current to the sensor. The drive circuit (70) includes detection means (77) for detecting an anomaly of the electrical connection state of the sensor, protection means (81), operable when the anomaly is detected, for forcedly switching to the protection mode, and report means (80) for outputting a report signal after the drive circuit has entered the protection mode. When the report is input, the signal output section outputs an instruction signal for switching the energization mode to the protection mode, and then outputs an instruction signal for switching to the drive mode. When the report signal is again input a predetermined number of times, the signal output section determines that an anomaly has occurred.

2 Claims, 4 Drawing Sheets

FIG. 3

| SWITCH | MODE | | |
|---|---|---|---|
| | PROTECTION MODE | NON-ACTIVE MODE | ACTIVE MODE |
| SW1 | OFF | ON | OFF |
| SW2 | | OFF | ON |
| SW3 | | OFF | ON |
| SW4 | | ON | OFF |
| SW5 | | ON | ON |
| SW6 | | ON (OFF) | ON |
| SW7 | | OFF (ON/OFF) | OFF |
| SW8 | | OFF (OFF/ON) | OFF |

NOTE: STATES IN PARENTHESES ARE THOSE DURING ACTIVATION DETERMIMATION

SENSOR CONTROL APPARATUS AND SENSOR CONTROL METHOD

BACKGROUND OF THE INVENTION

1. Field of the Invention

The present invention relates to a sensor control apparatus and a sensor control method for controlling the energization state of a sensor, such as a gas sensor including at least one cell which includes a solid electrolyte body and a pair of electrodes provided on the solid electrolyte body.

2. Description of the Related Art

An oxygen sensor, which detects the concentration of oxygen within an exhaust gas, is known as a gas sensor used for improving the fuel consumption of an internal combustion engine of an automobile or the like and/or for performing combustion control for the engine. Further, there has been a demand for reducing the amount of nitrogen oxides ($NO_X$) within exhaust gas in order to cope with stricter automobile exhaust gas regulations, and $NO_X$ sensors which can directly measure $NO_X$ concentration have been developed.

Such a gas sensor includes a gas sensor element having one or more cells each composed of oxygen-ion conductive solid electrolyte layer formed of zirconia or the like, and a pair of electrodes formed on the surface of the solid electrolyte layer. The gas sensor is configured to detect the concentration of a specific gas based on the output from the gas sensor element.

One known example of such a gas sensor is a full-range air-fuel-ratio sensor (hereinafter also referred to as a "UEGO sensor"), which is configured such that two cells (an oxygen-concentration detection cell and an oxygen pump cell) are arranged with a measurement chamber disposed therebetween, and a gas to be measured (hereinafter referred to as an "object gas") is introduced into the measurement chamber via a diffusion resistance so as to detect oxygen contained in the object gas. Further, another known example of such a gas sensor is an $NO_X$ gas sensor which includes three cells in total; i.e., the above-described two cells (an oxygen-concentration detection cell and an oxygen pump cell), and a cell for detecting $NO_X$ gas concentration.

A sensor drive circuit is connected to such a gas sensor so as to supply electric current to the sensor cells via the sensor drive circuit, and the concentration of a specific gas contained in the object gas is measured based on the output of a sensor cell. A control apparatus, including the sensor drive circuit, is called a "gas sensor control apparatus." Further, there are various states in which electric current is supplied to sensor cells (hereinafter referred to "energization states"), including an energization state for protecting the gas sensor; a pre-activation energization state in which a minute current is supplied to the gas sensor in a non-activated state; and an energization state for measuring the concentration of a specific gas.

Of these energization states, the energization state for protecting the gas sensor is established in an operation mode in which electric continuity between the sensor cells and the sensor drive circuit is cut off so as to stop the flow of current to the gas sensor and thereby protect the gas sensor. Further, the pre-activation energization state is established in an operation mode in which a minute current is supplied to the oxygen-concentration detection cell. As a result, oxygen of a reference concentration accumulates in a reference oxygen chamber of the oxygen-concentration detection cell, to thereby provide a reference for gas concentration measurement.

Incidentally, wiring lines (electric current supply lines) of the gas sensor or the sensor drive circuit may suffer a wiring anomaly, such as wire breakage or short circuiting with a battery or ground. When, irrespective of the occurrence of such a wiring anomaly, the energization state for gas concentration measurement is continued so as to measure the concentration of the specific gas, an excessively large current flows through the gas sensor, and the gas sensor (cells) may break.

In view of the above, a technique has been developed for cutting off the electrical connection between the sensor drive circuit and the gas sensor upon detecting a wiring anomaly so as to bring the gas sensor into a protected energization state, and then diagnosing the wiring anomaly so as to determine the details and location of the anomaly (see Patent Document 1). This technique prevents excessive current from continuously flowing to the gas sensor, to thereby prevent breakage of the gas sensor.

Further, when an instruction switching the energization state for gas concentration measurement from another energization state is output to the sensor drive circuit without awareness of a wiring anomaly, similarly, an excessively large current flows to the gas sensor, and the gas sensor may break.

In view of the above, a technique has also been developed which permits switching to the energization state for gas concentration measurement only when the state immediately before switching is the pre-activation energization state, to thereby allow for detection of an anomaly without breaking the gas sensor (see Patent Document 2). Even in the case where a wiring anomaly has occurred, if such a wiring anomaly is detected in the pre-activation energization state, in which a minute current is supplied to the gas sensor, the wiring anomaly can be detected. This is because a voltage generated in the gas sensor deviates from a normal range, without excessive current flowing through the gas sensor.

[Patent Document 1] Japanese Patent No. 3833687
[Patent Document 2] Japanese Patent Application Laid-Open (kokai) No. 2008-70194

3. Problems to be Solved by the Invention

A conventional gas sensor control apparatus is configured such that, even when a wiring (electric current supply line) anomaly is detected only once, the gas sensor control apparatus immediately determines that an anomaly has occurred, and stops operation of the sensor or switches the energization state of the sensor to an energization state for protection. However, the gas sensor control apparatus may erroneously detect an anomaly, despite the wiring being normal. Further, in some cases, a wiring anomaly such as wire breakage occurs temporarily, and the wiring anomaly suddenly disappears. Therefore, if operation of the sensor is stopped every time an anomaly is detected, wasteful time is needed to return to a gas-concentration-measurement operation. In particular, erroneous detection of a wiring anomaly tends to occur in association with short circuiting.

Further, in the case where the conventional gas sensor control apparatus is modified so as to check whether or not a wiring anomaly is detected through erroneous detection, a new energization state and an additional circuit must be provided. In such a case, the sensor drive circuit has a problem in that it requires additional circuit components, etc., whereby the size of the circuit increases.

SUMMARY OF THE INVENTION

It is therefore an object of the present invention to provide a sensor control apparatus which is less likely to erroneously detect an anomaly of an electrical connection state of a sensor, and which enables the sensor to quickly return to operation for gas concentration measurement when a temporary anomaly disappears.

The above object of the invention has been achieved by providing a sensor control apparatus comprising a signal output section which has a plurality of energization modes for a sensor that is to be connected to the sensor control apparatus, the energization modes including at least a drive mode for supplying electric current to the sensor and a protection mode for stopping the supply of electric current to the sensor to thereby protect the sensor, and which outputs an instruction signal for selecting one of the plurality of energization modes; and a sensor drive circuit for connection to the sensor and which enters one of the plurality of energization modes, when the sensor drive circuit receives an instruction signal from the signal output section, so as to control the supply of electric current to the sensor. The sensor drive circuit comprises detection means for detecting, in the drive mode, an anomaly of the state of electrical connection between the sensor drive circuit and the sensor; protection means, operable when the detection means detects an anomaly of the connection state, for forcing the sensor drive circuit to enter the protection mode irrespective of the energization mode in which the sensor drive circuit has operated; and report means for reporting to the signal output section that the sensor drive circuit is in the protection mode, after the sensor drive circuit is forced to enter the protection mode by the protection means. The signal output section comprises return means, operable when a report signal outputted by the report means is input to the signal output section, for outputting an instruction signal which instructs the sensor drive circuit to enter the protection mode, and then outputting an instruction signal which instructs the sensor drive circuit to enter the drive mode; and anomaly determination means for determining that an anomaly of the connection state has occurred, if the report signal is input again a predetermined number of times after the sensor drive circuit has entered the drive mode in response to the instruction signal output from the return means.

In the sensor control apparatus having the above-described configuration, if an anomaly of the electrical connection state of the sensor is detected only one time, the anomaly is not determined to have actually occurred, and operation of the sensor is not stopped immediately. Instead, the supply of electric current to the sensor is resumed, and the presence/absence of the anomaly is detected again. Thus, it is possible to prevent erroneous detection of an anomaly of the electrical connection state of the sensor (in other words, an anomaly of electric current supply lines), and to prevent operation of the sensor from being uselessly stopped when the anomaly suddenly disappears.

Furthermore, in the sensor control apparatus of the present invention, the anomaly determination means may determine that the anomaly of the connection state has occurred, when a phenomenon, in which the report signal is input again after the sensor drive circuit has entered the drive mode in response to the instruction signal output from the return means, occurs repeatedly a predetermined number of times which is set to two or more times.

By virtue of this configuration, after an anomaly of the electrical connection state of the sensor is detected, the process (in which the supply of electric current to the sensor is resumed and the presence/absence of the anomaly is detected again) is repeated two or more times. Therefore, erroneous detection of an anomaly or detection of a temporary anomaly can be avoided more reliably. Moreover, a situation can be avoided in which operation of the sensor is stopped every time an anomaly is detected, where the sensor requires a wasteful time to return to operation for gas concentration measurement.

According to the present invention, an anomaly of the electrical connection state of the sensor is less likely to be erroneously detected, and, when a temporary anomaly disappears, the sensor can be quickly returned to operation for gas concentration measurement.

BRIEF DESCRIPTION OF THE DRAWINGS

FIG. 3 is a Table showing the on-off sates of switches in respective energization modes.

DESCRIPTION OF REFERENCE NUMERALS

Figure 1:
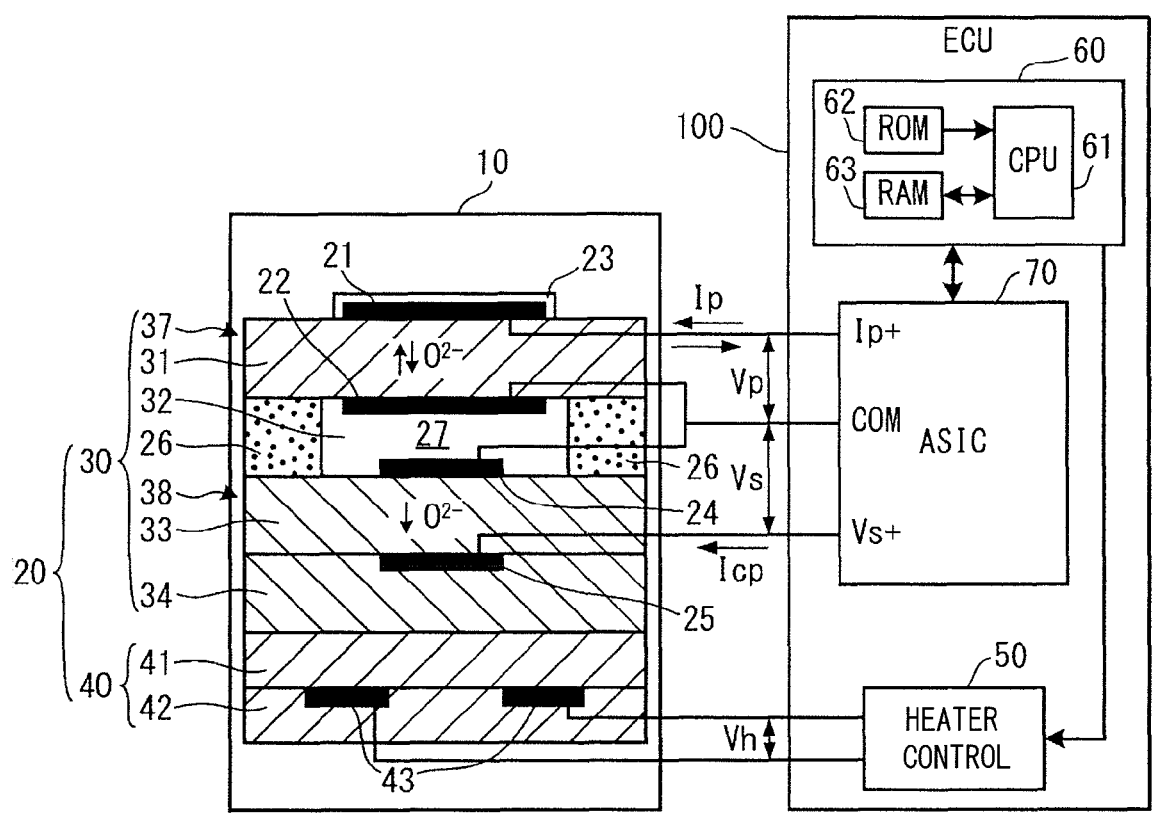
FIG. 1 is a diagram schematically showing the configuration of a full-range air-fuel-ratio sensor and a sensor control apparatus according to an embodiment of the invention.

Reference numerals used to identify various features in the drawings include:
10: full-range air-fuel-ratio sensor (sensor)
60: microcomputer (signal output section, return means, anomaly determination means)
70: ASIC (sensor drive circuit)
77: port anomaly detection circuit (detection means)
78: power-supply-voltage comparison circuit (detection means)
80: communication circuit (report means)
81: switch control circuit (protection means)
100: ECU (sensor control apparatus)

DETAILED DESCRIPTION OF THE PREFERRED EMBODIMENTS

An embodiment of the present invention will now be described with reference to the drawings. However, the present invention should not be construed as being limited thereto.

FIG. 1 is a block diagram of a sensor control apparatus 100 according to the embodiment of the present invention. The sensor control apparatus (electronic control unit (ECU)) 100 is connected to a full-range air-fuel-ratio sensor (corresponding to the "sensor" in the claims) 10, which is an example gas sensor. The ECU 100 includes a microcomputer (corresponding to the "signal output section," "return means," and "anomaly determination means" of the present invention) 60, an ASIC (corresponding to the "sensor drive circuit" of the present invention) 70, and a heater drive circuit 50.

In the ECU 100, the ASIC 70 and the heater drive circuit 50, which are incorporated in the ECU 100, control supply of electric current to the full-range air-fuel-ratio sensor 10. The ECU 100 detects an oxygen concentration (air-fuel ratio) on the basis of an output from the full-range air-fuel-ratio sensor 10, and performs air-fuel-ratio feedback control for an engine of an automobile based on the detected oxygen concentration.

First, the structure of the full-range air-fuel-ratio sensor 10 will be described. The full-range air-fuel-ratio sensor 10 is attached to an exhaust passage (not shown) of the engine, and substantially linearly detects the concentration of oxygen contained in exhaust gas passing through the exhaust passage. The full-range air-fuel-ratio sensor 10 has a structure in which an elongated plate-shaped sensor element 20 is held within an unillustrated housing. Signal wires for taking out a signal output from the sensor element 20 extend from the full-range air-fuel-ratio sensor 10, and are electrically connected to the ECU 100 mounted at a location remote from the full-range air-fuel-ratio sensor 10.

Next, the structure of the sensor element 20 will be described. The sensor element 20 is composed of a gas detection element 30 for detecting the oxygen concentration of the exhaust gas, and a heater element 40 for heating the gas detection element 30. The gas detection element 30 has a structure in which solid electrolyte bodies 31, 33 and 34 mainly formed of zirconia, and an insulating substrate 32 mainly formed of alumina are stacked in the order of the solid electrolyte bodies 34 and 33, the insulating substrate 32, and the solid electrolyte body 31. Paired electrodes 21 and 22 mainly formed of platinum are formed on opposite sides of the solid electrolyte body 31, and the surface of the electrode 21 is covered with a porous protection layer 23 formed of ceramic. This protection layer 23 protects the electrode 21 from poisoning components, such as silicon, contained in the exhaust gas. Furthermore, paired electrodes 24 and 25 are formed on opposite sides, respectively, of the solid electrolyte body 33. Of these electrodes, the electrode 25 is sandwiched between the solid electrolyte bodies 33 and 34, and is buried in the solid electrolyte bodies. Each of the solid electrolyte bodies 31, 33 and 34 and the insulating substrate 32 is in the form of an elongated plate, and FIG. 1 shows a cross section of the sensor element 20 taken perpendicular to the longitudinal direction thereof.

At one end of the insulating substrate 32 with respect to the longitudinal direction thereof, a gas detection chamber 27 is formed, which is a hollow internal space whose opposite wall surfaces are formed by corresponding surfaces of the solid electrolyte bodies 31 and 33 and into which the exhaust gas can be introduced. Porous diffusion-rate-limiting sections 26 are provided at opposite ends of the gas detection chamber 27 with respect to the width direction so as to limit the flow rate of exhaust gas introduced into the gas detection chamber 27. The electrode 22 on the solid electrolyte body 31 and the electrode 24 on the solid electrolyte body 33 are exposed to the interior of the gas detection chamber 27.

The heater element 40 has a structure in which two insulating substrates 41 and 42 mainly formed of alumina and assuming the form of a plate are stacked, and a heat generation resistor 43 mainly formed of platinum is interposed between the two insulating substrates. It is known that, although a solid electrolyte body formed of zirconia exhibits insulating properties at room temperature, it is activated and exhibits oxygen ion conductivity in a high-temperature atmosphere. The heater element 40 is provided so as to heat and activate the solid electrolyte bodies 31 and 33. This heater element 40 is provided, as an outer layer, on the side of the gas detection element 30 where the solid electrolyte body 34 is present. The insulating substrate 41 of the heater element 40 and the solid electrolyte body 34 of the gas detection element 30 are united.

In the sensor element 20 having the above-described structure, the solid electrolyte body 31 and the pair of electrodes 21 and 22 provided on the opposite surfaces thereof function as an oxygen pump cell which pumps oxygen into the gas detection chamber 27 from outside the sensor element 20 or pumps oxygen out of the gas detection chamber 27 to the outside. In the following description, the oxygen pump cell composed of the solid electrolyte body 31 and the electrodes 21 and 22 will be referred to as an Ip cell 37.

Furthermore, the solid electrolyte body 33 and the pair of electrodes 24 and 25 provided on the opposite surfaces thereof function as an oxygen concentration detection cell which generates an electromotive force in accordance with a difference in oxygen concentration between the electrodes. A very small constant current is caused to flow between the paired electrodes 24 and 25, whereby oxygen of a certain amount is supplied from the electrode 24 side to the electrode 25 side via the solid electrolyte body 33. The electrode 25 functions as an oxygen reference electrode which serves as a reference for detecting oxygen concentration within the gas detection chamber 27. In the following description, the oxygen concentration detection cell composed of the solid electrolyte body 33 and the electrodes 24 and 25 will be referred to as a Vs cell 38. The specific functions of the Ip cell 37 and the Vs cell 38 are described below.

Next, the configuration of the ECU 100, to which the sensor element 20 is connected, will be described. The ECU 100 includes various circuits (devices) associated with control of the engine, in addition to the microcomputer 60, the ASIC 70 and the heater drive circuit 50. The microcomputer 60 controls the supply of electric power to the full-range air-fuel-ratio sensor 10 via the ASIC 70 and the heater drive circuit 50, and receives from the sensor element 20 a voltage signal representing a current value corresponding to the oxygen concentration of the exhaust gas.

The microcomputer 60 is a device for electronically controlling the drive of the engine of the automobile, etc., and controls, in accordance with various control programs, various circuits (devices), including the ASIC 70, which are connected to the microcomputer 60, to thereby control injection timing of fuel and ignition timing. For such operation, via an unillustrated signal input/output section, the microcomputer 60 sends instructions to the ASIC 70 and the heater drive circuit 50, and receives an output (detection signal) of the full-range air-fuel-ratio sensor 10 via the ASIC 70. Furthermore, the microcomputer 60 receives information representing, for example, combustion pressure and crank angle from which the piston position and rotational speed of the engine can be detected.

The microcomputer 60 includes a CPU 61 having a known configuration, a ROM 62, and a RAM 63. The CPU 61 executes various controls including the above-described control. The ROM 62 stores programs, initial values, etc., for performing these various controls. The RAM 63 temporarily stores various variables, flags, counters, etc., which are used for execution of the programs.

The ASIC 70 is an application specific integrated circuit in which circuits for driving and controlling the full-range air-fuel-ratio sensor 10 are integrated into a single chip, to thereby facilitate incorporation of the circuits into the ECU 100. The ASIC 70 controls the supply of electric current to the gas detection element 30, and outputs to the microcomputer 60 a detection signal representing the oxygen concentration detected via the gas detection element 30. As described in detail below, the ASIC 70 detects the electromotive force Vs generated between the electrodes 24 and 25 of the Vs cell 38, and compares it with a predetermined reference voltage (e.g., 450 mV). The ASIC 70 controls, on the basis of the result of the comparison, the flow direction and magnitude of the pump current Ip flowing between the electrodes 21 and 22 of the Ip cell 37, to thereby cause the Ip cell 37 to pump oxygen into the gas detection chamber 27 or pump oxygen out of the gas detection chamber 27. Furthermore, the ASIC 70 converts the current flowing through the Ip cell 37 to a voltage, and outputs the voltage to the microcomputer 60 as a detection signal representing the oxygen concentration. Moreover, the ASIC 70 separately detects the resistance (impedance) of the gas detection element 30 (Vs cell 38), which changes with temperature, and outputs the resistance to the microcomputer 60.

In the present embodiment, transmission and reception of various signals between the microcomputer 60 and the ASIC 70 are performed by means of clock synchronization communication. Also, the microcomputer 60 performs the clock synchronization communication between the same and other circuits (devices), other than the ASIC 70, which are connected to the microcomputer 60. Therefore, the microcomputer 60 sequentially selects the circuits one at a time, through switching, as a connection counterpart, and sends a signal to and receives a signal from the circuit selected as a connection counterpart in a synchronized manner. Thus, the microcomputer 60 sends control-related instruction signals to the various circuits, and receives control-related information from the circuits. Notably, as described below, information representing the oxygen concentration detected by the gas detection element 30 and a detected resistance value used for activation determination, etc., is input to the microcomputer 60 via a transmission line different from that for the clock synchronization communication.

The heater drive (control) circuit 50 is connected to opposite ends of the heat generation resistor 43 of the heater element 40 provided in the sensor element 20. The heater drive circuit 50 is configured to electrically connect one end of the heat generation resistor 43 to a battery, and to electrically connect the other end of the heat generation resistor 43 to ground. This heater drive circuit 50 includes a switching element (not shown) which is disposed between the battery and the one end of the heat generation resistor 43 and which controls the supply of electric current to the heat generation resistor 43 by means of PWM control (pulse width modulation control). The duty ratio of the voltage waveform of a voltage Vh applied between the opposite ends of the heat generation resistor 43 is computed by the CPU 61 of the microcomputer 60. Specifically, the duty ratio of the voltage waveform of the voltage Vh applied to the heat generation resistor 43 is computed based on the resistance of the Vs cell 38 detected by the ASIC 70 and the voltage of the battery (power supply voltage) such that the resistance of the Vs cell 38 reaches a target resistance as a result of heating by the heat generation resistor 43. The microcomputer 60 turns the switching element on and off based on the computed duty ratio, whereby the voltage (effective voltage) Vh corresponding to the duty ratio is applied to the heat generation resistor 43. Thus, the Ip cell 37 and the Vs cell 38 are heated.

Next, the electrical configuration of the above-mentioned ASIC 70 will be described with reference to FIG. 2.

As described with reference to FIG. 1, of the electrodes of the Ip cell 37 and the Vs cell 38 of the full-range air-fuel-ratio sensor 10, the electrodes 22 and 24 of the two cells exposed to the gas detection chamber 27 are electrically connected to each other. As shown in FIG. 2, these electrodes 22 and 24 connected together are connected to a COM port of the full-range air-fuel-ratio sensor 10. The electrode 25 of the Vs cell 38, which is not exposed to the gas detection chamber 27, is connected to a Vs+ port of the full-range air-fuel-ratio sensor 10, and serves as the above-mentioned oxygen reference electrode. The electrode 21 of the Ip cell 37, which is not exposed to the gas detection chamber 27, is connected to an Ip+ port of the full-range air-fuel-ratio sensor 10, and carries out oxygen exchange between the gas detection chamber 27 and the outside atmosphere.

The ECU 100 includes A/D converters 98 and 99, a resistor R1, and a detection resistor Rd, in addition to the above-described microcomputer 60, ASIC 70 and heater drive circuit 50 (heater control 50). The A/D converters 98 and 99 are connected to a Vout port and a Vrpvs port (described below), respectively, of the ASIC 70, and convert analog output voltages supplied from these ports to corresponding digital values and each outputs the digital values to the CPU 61 of the microcomputer 60. Furthermore, as described above, the heater drive circuit 50 supplies electric current from the battery to the heat generation resistor 43, while performing PWM control in accordance the duty ratio instructed by the CPU 61.

The ASIC 70 includes a plurality of input/output ports (Vs+, Pout, Vcent, COM, Ip+, Bat, Vout, Vrpvs). The corresponding ports (i.e., the Vs+ port, the COM port, and the Ip+ port) of the full-range air-fuel-ratio sensor 10 are connected to the Vs+ port, the COM port and the Ip+ port, respectively, of the ASIC 70. The ASIC 70 includes an Icp supply circuit 74, a −Iconst supply circuit 75 and a +Iconst supply circuit 76, which are connected to the Vs+ port via switches SW5, SW7 and SW8, respectively. The Icp supply circuit 74 supplies a very small constant current Icp to the gas detection element 30 (specifically, the Vs cell 38) of the full-range air-fuel-ratio sensor 10. The −Iconst supply circuit 75 supplies a constant current −Iconst for measurement of the resistance (impedance) of the Vs cell 38. The +Iconst supply circuit 76 supplies a constant current +Iconst whose polarity is opposite that of the constant current −Iconst.

The ASIC 70 also includes an operational amplifier OP1 for supplying a pump current Ip to the Ip cell 37 of the gas detection element 30 in an active mode described below, and a voltage division circuit 85 and an operational amplifier OP2 for supplying a current for detection of an anomaly of the port voltage. The inverting input (−) terminal of the operational amplifier OP1 is connected to the Vcent port, and is also connected to the COM port via the resistor R1. A reference voltage of 3.6 V is applied to the non-inverting input (+) terminal of the operational amplifier OP1, and the output terminal of the operational amplifier OP1 is connected to the Ip+ port via a switch SW3. The voltage division circuit 85, which includes voltage division resistors R2 and R3, is connected to the Ip+ port via a SW4, whereby the potential of the Ip+ port is maintained at 2.5 V. Meanwhile, the reference voltage of 3.6 V is applied to the non-inverting input (+) terminal of the operational amplifier OP2, and the inverting input (−) terminal of the operational amplifier OP2 is connected to its own output terminal. The output terminal of the operational amplifier OP2 is connected to the Vcent port via a switch SW1.

Moreover, the ASIC 70 includes a PID control circuit 71. In the active mode, the magnitude of the pump current Ip supplied from the operational amplifier OP1 to the Ip cell 37 is controlled by this PID control circuit 71. The input side of the PID control circuit 71 is connected to the Vs+ port via a buffer OP3. Specifically, the non-inverting input (+) terminal of the buffer OP3 is connected to the Vs+ port via a switch SW6. A capacitor C1 is connected to a line between the non-inverting input (+) terminal and the switch SW6. The output terminal of the buffer OP3 is connected to the inverting input (−) terminal, and is also connected to the input side of the PID control circuit 71. Moreover, a reference voltage generation circuit 72 for generating a reference voltage (450 mV), which serves as a control target of the pump current Ip, is connected to the input side of the PID control circuit 71. Meanwhile, the output side of the PID control circuit 71 is connected to the Pout port via a switch SW2, and is further connected to the Vcent port (i.e., the inverting input (−) terminal of the operational amplifier OP1) via the detection resistor Rd, described below.

The output terminal of the buffer OP3 is also connected to the input side of a second differential amplification circuit 82. The Vs+ port is also connected to the input side of this second differential amplification circuit 82. The input side of the second differential amplification circuit 82 is connected to the above-mentioned −Iconst supply circuit 75 via a switch SW7. The output side of the second differential amplification circuit 82 is connected to the input side of a sample hold circuit 83, and the output side of the sample hold circuit 83 is connected to the Vprvs port. Therefore, the output of the second differential amplification circuit 82 is input to the microcomputer 60 via the A/D converter 99. As described below, the determination as to whether or not the gas detection element 30 has been activated is made on the basis of the resistance (impedance) of the Vs cell 38 calculated from a change in voltage Vs between the opposite ends of the Vs cell 38 at a time when a constant current −Iconst for resistance measurement is supplied to the Vs cell 38. The second differential amplification circuit 82 detects a deviation ΔVs between the potential of the Vs+ port before the constant current −Iconst is supplied, and the potential of the Vs+ port after the constant current −Iconst is supplied for a predetermined period of time, and outputs the deviation ΔVs to the microcomputer 60 via the Vrpvs port. The sample hold circuit 83 has a known circuit configuration for holding the deviation ΔVs output from the second differential amplification circuit 82, and holds the deviation ΔVs detected at a given time until next detection of the deviation ΔVs, to thereby enable the CPU 61 to read the deviation ΔVs at a timing different from the timing of the detection.

The ASIC 70 further includes a first differential amplification circuit 73. The above-mentioned detection resistor Rd is provided so as to detect the magnitude of the pump current Ip, and its opposite ends are connected to the Pout port and the Vcent port. The Pout port and the Vcent port are connected to the first differential amplification circuit 73. The first differential amplification circuit 73 amplifies a potential difference Vd, which develops across the detection resistor Rd as a result of the pump current Ip flowing therethrough, at a predetermined amplification factor, and outputs the amplified potential difference from the Vout port to the microcomputer 60, as a detected potential Vout, via the A/D converter 98.

Also, the ASIC 70 includes a port anomaly detection circuit 77, a power-supply-voltage comparison circuit 78, a communication circuit 80 and a switch control circuit 81. The port anomaly detection circuit 77 compares the potentials of the Vs+ port, the COM port and the Ip+ port with a threshold value (voltage) set for anomaly direction, and detects the presence/absence of an anomalous state, such as a short circuit or wire breakage (anomaly of the electrical connection state of the sensor). When an anomaly of any one of the ports is detected, the port anomaly detection circuit 77 sends to the switch control circuit 81 a signal for instructing execution of switch control for a protection mode (described below) which control turns all the switches SW1 to SW8 off (that is, the ASIC 70 is forced to enter the protection mode). Furthermore, the port anomaly detection circuit 77 writes in a transmission buffer of the communication circuit 80 a signal (flag) reporting the occurrence of the port anomaly. This signal reporting the port anomaly is sent to the microcomputer 60 when clock synchronization communication is performed between the microcomputer 60 and the ASIC 70.

The power-supply-voltage comparison circuit 78 monitors the Bat port, and compares the power supply voltage supplied from the battery to the ECU 100 and the ASIC 70 with a reference potential. When the power supply voltage becomes lower than the reference potential, the power-supply-voltage comparison circuit 78 sends to the switch control circuit 81 a signal for instructing execution of switch control for the protection mode (described below) which control turns all the switches SW1 to SW8 off (that is, the ASIC 70 is forced to enter the protection mode). Furthermore, the power-supply-voltage comparison circuit 78 writes in the transmission buffer of the communication circuit 80 a signal (flag) reporting that the ASIC 70 has entered the protection mode. This signal is sent to the microcomputer 60 when the clock synchronization communication is performed. Notably, the port anomaly detection circuit 77 and the power-supply-voltage comparison circuit 78 correspond to the "detection means" in the present invention.

The communication circuit 80 is adapted to perform the above-described clock synchronization communication with the microcomputer 60. When the communication circuit 80 receives from the microcomputer 60 a device selection signal (a signal which instructs the communication circuit 80 to perform communication between the microcomputer 60 and the ASIC 70), in synchronism with the clock frequency of the microcomputer 60, the communication circuit 80 receives an instruction signal, etc., sent from the microcomputer 60, and stores these in a reception buffer. At the same time, the communication circuit 80 sends to the microcomputer 60 information which represents the presence/absence of an anomalous state detected by the anomaly detection circuit 77 and is written in the transmission buffer. When the communication circuit 80 receives an instruction signal from the microcomputer 60, the communication circuit 80 sends to the switch control circuit 81 a signal which instructs execution of a switch control corresponding to an energization mode instructed by the instruction signal. Notably, the communication circuit 80 corresponds to the "report means" of the present invention.

The switch control circuit 81 is adapted to individually turn the switches SW1 to SW8 on and off. When the switch control circuit 81 receives an instruction signal from the communication circuit 80, the port anomaly detection circuit 77, the power-supply-voltage comparison circuit 78, or the like, the switch control circuit 81 turns the switches on and off in accordance with the instructed energization mode. Notably, the switch control circuit 81 corresponds to the "protection means" of the present invention.

Next, energization modes which determine the on-off states of the switches SW1 to SW8 controlled by the switch control circuit 81 will be described with reference to FIGS. 2 and 3. FIG. 3 is a table showing the on-off states of the switches SW1 to SW8 in each energization mode. In the present embodiment, the energization modes for the full-range air-fuel-ratio sensor 10 include at least a protection mode and a drive mode. Further, a non-active mode and an active mode are used as the drive mode.

The "protection mode" is an energization mode in which the supply of electric current to the gas detection element 30 is stopped so as to protect the gas detection element 30. As shown in FIG. 3, in the protection mode, all the switches SW1 to SW8 are tuned off so that no electric current is supplied to the gas detection element 30.

The "non-active mode" is an energization mode in which, through supply of electric current to the heater element 40, the gas detection element 30 is heated so as to activate the same. In this energization mode, for the gas detection element 30, energization for activation determination; i.e., for determining whether or not the gas detection element 30 has been activated, and preliminary energization for accumulating oxygen in the oxygen reference electrode in preparation for detection of oxygen concentration are carried out. A voltage for detecting a port anomaly is applied to each of the ports linked to the gas detection element 30. Specifically, as shown in FIG. 3, in the non-active mode, the switches SW1, SW4, SW5 and SW6 are turned on, and the switches SW2, SW3, SW7 and SW8 are turned off. As a result, as shown in FIG. 2, the constant current Icp is supplied to the Vs cell 38, whereby oxygen accumulates in the oxygen reference electrode (the electrode 25). Furthermore, since the switches SW2 and SW3 are fixed to an off state, a large current for detection of oxygen concentration is not supplied to the Ip cell 37 from the PID control circuit 71 and the operational amplifier OP1. Since the switches SW1 and SW4 are turned on, the voltage of 3.6 V is applied to the Vcent port and the voltage of 2.5 V is applied to the Ip+ port. Thus, a state in which the port anomaly detection circuit 77 can detect port anomalies is established.

Notably, in the non-active mode, a determination is made as to whether or not the gas detection element 30 has been activated. In this case, the switch SW6 is turned off temporarily, and the on-off states of the switches SW7 and SW8 are changed in this state. This method of determining whether or not the gas detection element 30 has been activated will be described below.

The "active mode" is an energization mode in which the activated gas detection element 30 detects oxygen concentration. As shown in FIG. 3, the switches SW1, SW4, SW7 and SW8 are turned off, and the switches SW2, SW3, SW5 and SW6 are turned on. Thus, as shown in FIG. 2, in a state in which the supply of the constant current Icp to the Vs cell 38 is maintained, a large current for detection of oxygen concentration can be supplied from the PID control circuit 71 and the operational amplifier OP1 to the Ip cell 37.

Next, an operation of detecting the oxygen concentration of exhaust gas by use of the full-range air-fuel-ratio sensor 10 will be briefly described with reference to FIGS. 1 and 2. When the very small constant current Icp is supplied from the Icp supply circuit 74 to the Vs cell 38, through the solid electrolyte body 33, oxygen is pumped from the gas detection chamber 27 to the electrode 25 connected to the Vs+ port. As a result, the electrode 25 is exposed to a reference oxygen concentration. Furthermore, a voltage (electromotive force) Vs is generated between the electrodes 24 and 25 of the Vs cell 38 in accordance with the difference between the reference oxygen concentration and the oxygen concentration of the exhaust gas introduced into the gas detection chamber 27. The voltage (electromotive force) Vs generated in the Vs cell 38 is compared with a reference voltage of 450 mV, which corresponds to a voltage which is generated in the Vs cell 38 when the air-fuel ratio of the exhaust gas is equal to the theoretical air-fuel ratio, and the result of the comparison is fed back to the operational amplifier OP1 by the PID control circuit 71. In this manner, the flow direction and magnitude of the pump current Ip flowing through the Ip cell 37 is controlled by the PID control circuit 71 and the operational amplifier OP1, whereby pumping in or pumping out of oxygen by the Ip cell 37 is carried out such that the air-fuel ratio of the exhaust gas within the gas detection chamber 27 becomes equal to the theoretical air-fuel ratio.

Specifically, in the case where the air-fuel ratio of the exhaust gas having flowed into the gas detection chamber 27 is on the rich side in relation to the theoretical air-fuel ratio, since the oxygen concentration of the exhaust gas is low, the pump current Ip is controlled such that oxygen is pumped from the outside into the gas detection chamber 27 via the solid electrolyte body 31. Meanwhile, in the case where the air-fuel ratio of the exhaust gas having flowed into the gas detection chamber 27 is on the lean side in relation to the theoretical air-fuel ratio, since a large amount of oxygen is present in the exhaust gas, the pump current Ip is controlled such that oxygen is pumped out of the gas detection chamber 27 to the outside. At that time, the pump current Ip, which flows through the detection resistor Rd, is converted to a voltage by the first differential amplification circuit 73, which is then output, as the output (detection signal) of the full-range air-fuel-ratio sensor 10, to the CPU 61 of the microcomputer 60 via the A/D converter 98. The CPU 61 detects the concentration of oxygen contained in the exhaust gas from the magnitude and flow direction of the pump current Ip obtained as the detection signal.

In order to stably detect the oxygen concentration of the exhaust gas, the gas detection element 30 must be heated until the temperatures of the solid electrolyte bodies 31 and 33 become equal to an activation temperature (e.g., 750° C.) or higher, to thereby become activated. Therefore, before the operation of detecting the oxygen concentration is started, a determination is made whether or not the gas detection element 30 has been activated. Next, a method of determining whether or not the gas detection element 30 has been activated will be briefly described with reference to FIG. 2.

Since the oxygen concentration at the electrode 25 (oxygen reference electrode) must be increased to the reference oxygen concentration before performing the oxygen concentration detection operation, in the non-active mode of the gas detection element 30, the switch SW5 is turned on so as to supply the constant current Icp to the Vs cell 38 (preliminary energization). Furthermore, in the non-active mode, the switches SW1 and SW4 are turned on so as to enable the port anomaly detection circuit 77 to monitor the potentials of the Vs+ port, the COM port and the Ip+ port for detection of a failure such as a short circuit or wire brakeage.

The determination as to whether or not the gas detection element 30 has been activated is performed on the basis of the resistance (impedance) of the Vs cell 38 calculated from a change in the voltage Vs between the opposite ends of the Vs cell 38 at the time when the constant current −Iconst for resistance measurement is supplied to the Vs cell 38. This determination is periodically performed during the non-active mode. Specifically, as shown in FIG. 3, the switch SW6 is turned off, whereby the potential of the Vs+ port at the time when only the constant current Icp is supplied is held by the capacitance C1. The held potential is input to the second differential amplification circuit 82 by the buffer OP3. The switch SW7 is then turned on, whereby the constant current −Iconst is superposed on the constant current Icp, and the potential generated at the Vs+ port is input to the second differential amplification circuit 82. Accordingly, the second differential amplification circuit 82 outputs the deviation ΔVs between the potential of the Vs+ port generated as a result of supply of the constant current Icp to the Vs cell 38 and the potential of the Vs+ port having changed as a result of superposition of the constant current −Iconst. The deviation ΔVs is input to the microcomputer 60 via the sample hold circuit 83, the Vrpvs port and the A/D converter 99. The microcomputer 60 calculates the resistance (impedance) of the Vs cell 38 from the deviation ΔVs and the constant current −Iconst, and compares the calculated resistance with an activation determination threshold value, to thereby determine whether or not the Vs cell 38 (accordingly, the gas detection element 30) has been activated.

Notably, the constant current −Iconst is supplied to the Vs cell 38 for a predetermined short period of time after the switch SW7 is turned on. When the switch SW7 is turned off after that, the output of the second differential amplification circuit 82, which represents the deviation ΔVs, is held by the sample hold circuit 83. Subsequently, the switch SW8 is turned on so as to supply the constant current +Iconst of opposite polarity to the Vs cell 38. This operation is performed to enable the Vs cell 38 to return to an ordinary state, within a short period of time, from a state in which it has been influenced by an orientation phenomenon associated with the oxygen ion conductivity of the solid electrolyte body. After the deviation ΔVs is obtained, the on-off states of the switches SW1 to SW8 are returned to those set for the non-active mode. Notably, although not shown in FIG. 3, even after the ASIC 70 enters the active mode, the periodic determination as to whether or not the gas detection element 30 has been activated is continued, and operation of the switches SW6 to SW8 as described above is performed.

As described above, the supply of electric current to the full-range air-fuel-ratio sensor 10 is controlled by the ASIC 70 in accordance with the energization mode instructed by the microcomputer 60 of the ECU 100. As described above, in the non-active mode, the ASIC 70 monitors the Vs+ port, the COM port and the Ip+ port connected to the gas detection element 30. When an anomaly, such as a short circuit, wire breakage, or the like is detected, irrespective of the current energization mode, the ASIC 70 turns all the switches SW1 to SW8 off, whereby the ASIC 70 enters the protection mode. Furthermore, the ASIC 70 reports to the microcomputer 60 that the ASIC 70 has entered the protection mode.

Figure 4:
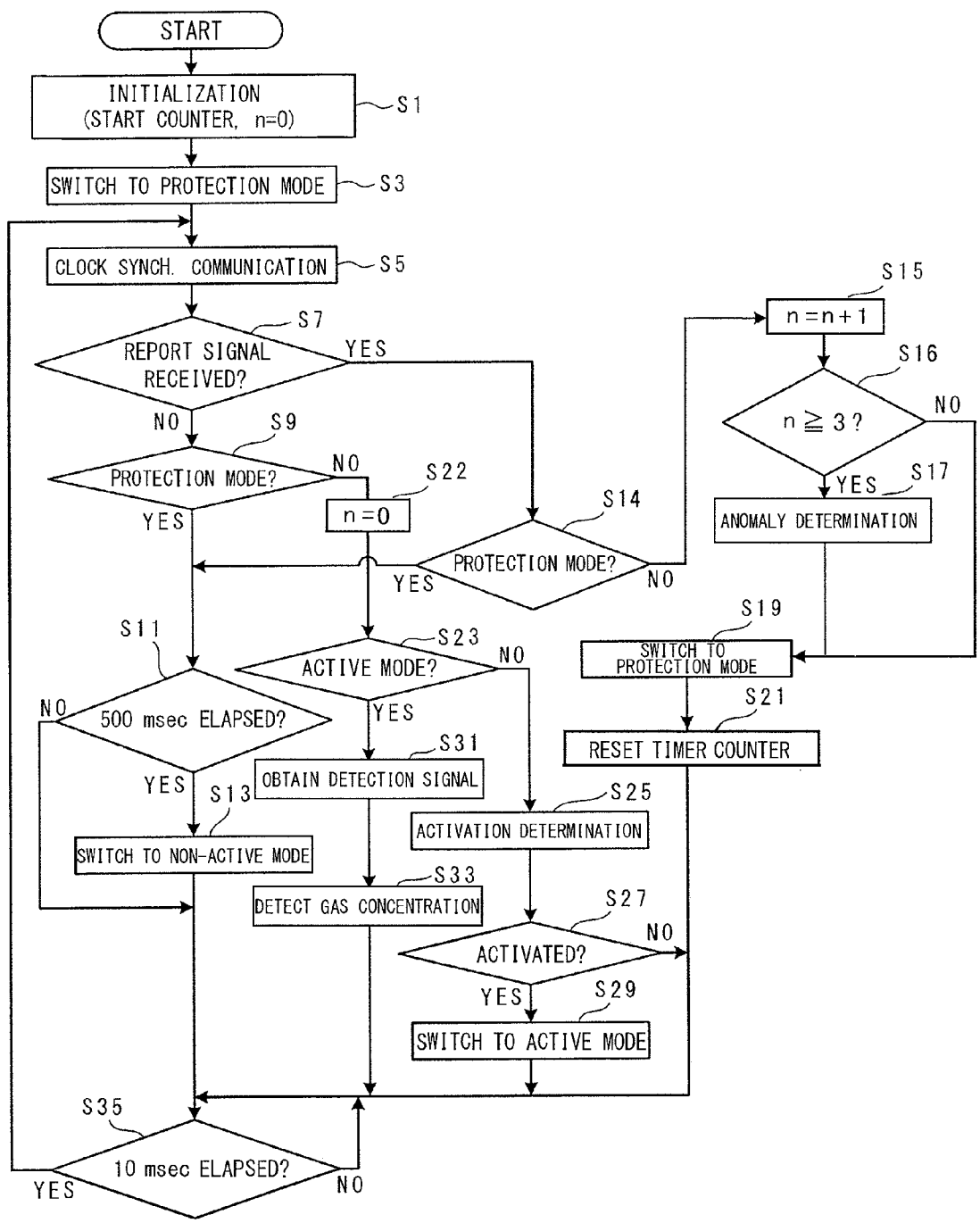
FIG. 4 is a flowchart showing an energization control program.

The reporting to the microcomputer 60 that the ASIC 70 has entered the protection mode is carried out by transmitting to the microcomputer 60 a signal (report signal) reporting that the ASIC 70 has entered the protection mode, when the clock synchronization communication is first performed after the ASIC 70 has entered the protection mode. Specifically, a specific one bit of data sent from the ASIC 70 by means of the clock synchronization communication corresponds to the report signal. Upon receipt of the report signal, the microcomputer 60 performs the control for the ASIC 70 after returning the control to the initial state; i.e., a state at the time the power is turned on. The control of the ASIC 70 in the microcomputer 60 is performed in accordance with an energization control program performed by the CPU 61. Next, operation of the energization control program will be described with reference to FIGS. 2 to 4. FIG. 4 is a flowchart of the energization control program.

Notably, in the energization control program, a mode flag is used so as to represent the present energization mode, which is the protection mode, the non-active mode, or the active mode. In the following description, each step of the flowchart is abbreviated to "S."

The CPU 61 executes the energization control program shown in FIG. 4, along with other programs for controlling the internal combustion engine, when the ignition switch of the automobile is turned on, whereby drive of the microcomputer 60 of the ECU 100 is started. The CPU 61 is first initialized so as to secure on the RAM 63 areas for flags, variables, counters, etc., used in the energization control program, to reset these, and to set initial values (S1). Also, the CPU 61 starts a counter which is used for determination processing based on elapse of time. Furthermore, the CPU 61 resets an anomaly determination counter n to zero. This anomaly determination counter n is used for performing the processing of determining an anomaly of the electrical connection state (wiring anomaly) of the sensor, described below. The anomaly determination counter n represents the number of times the ASIC 70 has entered the protection mode.

Next, in order to instruct the ASIC 70 to enter the protection mode, the CPU 61 stores an instruction signal in a transmission buffer, which stores information transmitted by the clock synchronization communication. The CPU 61 then changes the value of the mode flag so as to indicate that the present energization mode is the protection mode (S3). When a communication channel is established between the microcomputer 60 and the ASIC 70 as a result of generation of the device selection signal, by means of the clock synchronization communication, the CPU 61 instructs the ASIC 70 to enter the protection mode (S5).

As a result, an instruction signal which instructs the ASIC 70 to enter the protection mode is stored in the reception buffer of the communication circuit 80 of the ASIC 70 by means of the clock synchronization communication. In response thereto, the communication circuit 80 sends to the switch control circuit 81 a signal which instructs execution of the switch control for the protection mode. In accordance with this instruction, the switch control circuit 81 executes the switch control for the protection mode shown in FIG. 3, to thereby turn all the switches SW1 to SW8 off.

Next, as shown in FIG. 4, in the microcomputer 60 of the ECU 100, the CPU 61 checks a reception buffer so as to determine whether or not a report signal was received from the ASIC 70 during the clock synchronization communication performed in S5 (S7).

After the power is on, the ASIC 70 enters the protection mode to thereby turn all the switches SW1 to SW8 off. At that time, all the Vs+ port, the COM port, and the Ip+ port are brought into a high impedance state. Therefore, the port anomaly detection circuit 77 determines that an anomaly has occurred in the circuit, and stores in the transmission buffer of the communication circuit 80 a report signal reporting an anomaly of the ports. Therefore, in S7 of FIG. 4, the CPU 61 receives the report signal from the ASIC 70 via the clock synchronization communication (S7: YES). When the CPU 61 receives the report signal in S7, the CPU 61 proceeds to S14. So long as the present energization mode is the protection mode (S14: YES), the CPU 61 ignores the report signal, and proceeds to S11. Moreover, in the case where the CPU 61 does not receive the report signal in S7 (S7: NO), if the present energization mode is the protection mode (S9: YES), the CPU 61 proceeds to S11.

In S11, the CPU 61 determines whether or not a predetermined period of time has elapsed after the counter has been started. In the present embodiment, an elapse of 500 msec is set as an example condition for switching the energization mode from the protection mode to the non-active mode. Since the present point in time is immediately after the start of the drive, 500 msec has not yet elapsed (S11: NO). Therefore, in S35, the CPU 61 determines, by making use of the abovementioned counter, whether or not a time corresponding to the repetition interval (10 msec in the present embodiment) of the program has elapsed, and waits until the time corresponding to the repetition interval elapses (S35: NO). After waiting, the CPU 61 returns to S5 (S35: YES), and repeats S5 to S35 to thereby continue the protection mode.

When 500 msec has elapsed while S5, S7, S9, S11, and S35 are repeated (S11: YES), the CPU 61 stores in the transmission buffer an instruction signal to instruct the ASIC 70 to enter the non-active mode (S13). Also, the CPU 61 changes the value of the mode flag so as to indicate that the present energization mode is the non-active mode. The CPU 61 then returns to S5 after waiting 10 msec (S35: NO) as in the above-described case. When the communication between the microcomputer 60 and the ASIC 70 is established by the device selection signal, an instruction signal which instructs the ASIC 70 to enter the non-active mode is sent by the clock synchronization communication.

Upon receipt of the instruction signal which instructs the ASIC 70 to enter the non-active mode, the communication circuit 80 of the ASIC 70 sends to the switch control circuit 81 a signal which instructs execution of the switch control for the non-active mode. In accordance with this instruction, the switch control circuit 81 executes the switch control for the non-active mode shown in FIG. 3, to thereby turn the switches SW2, SW3, SW7 and SW8 off, and to turn the switches SW1, SW4, SW5 and SW6 on. As shown in FIG. 2, the constant current Icp is supplied to the Vs cell 38 of the gas detection element 30, and the operational amplifier OP2 and the voltage division circuit 85 are connected to the COM port and the Ip+ port. As a result, the Vs+ port, the COM port, and the Ip+ port have respective potentials, and are no longer in the high impedance state. Thus, a state is established in which the port anomaly detection circuit 77 can properly perform port anomaly detection; i.e., can determine whether or not an anomaly, such as a short circuit or wire breakage, has occurred. Accordingly, when a short circuit, wire breakage, or the like has not actually occurred, the generation of the report signal reporting a port anomaly is stopped. However, when a port anomaly is detected, a signal which reports the port anomaly is written in the transmission buffer of the communication circuit 80, and is sent to the microcomputer 60 when the clock synchronization communication is performed the next time.

As shown in FIG. 4, in the microcomputer 60 of the ECU 100, the CPU 61 operates as follows. When the CPU 61 does not receive the report signal (S7: NO), the CPU 61 proceeds S9, and determines that the present energization mode is not the protection mode. This is because the value of the mode flag represents the non-active mode (S9: NO). In such a case, the CPU 61 sets the anomaly determination counter, which indicates the number of times the ASIC 70 entered the protection mode, to 0 (n=0) (S22). Moreover, after S22, the CPU 61 checks the mode flag and determines whether or not the present energization mode is the active mode (S23). Since the ASIC 70 having been in the protection mode enters the non-active mode (S23: NO), the CPU 61 performs activation determination processing (S25). That is, the CPU 61 executes a program separately from the energization control program so as to supply the constant current −Iconst for resistance measurement to the Vs cell 38 and to determine whether or not the gas detection element 30 has been activated, on the basis of a change in the obtained deviation ΔVs. When the CPU 61 determines that the gas detection element 30 has not yet been activated (S27: NO), the CPU 61 proceeds to S35 so as to wait an elapsed time of 10 msec, and then returns to S5 so as to repeat S5 to S35.

After that, S5, S7, S9, S23, S25, S27 and S35 are repeated, and the non-active mode is continued until the CPU 61 determines that the gas detection element 30 has been activated. When the CPU 61 determines that the gas detection element 30 has been activated (S27: YES), the CPU 61 stores an instruction signal in the transmission buffer so as to instruct the ASIC 70 to enter the active mode (S29). Also, the CPU 61 changes the value of the mode flag so as to indicate that the present energization mode is the active mode. Subsequently, when the communication between the microcomputer 60 and the ASIC 70 is established by the device selection signal at the time of next execution of S5, the instruction signal which instructs the ASIC 70 to enter the active mode is sent by the clock synchronization communication.

Upon receipt of the instruction signal which instructs the ASIC 70 to enter the active mode, the communication circuit 80 of the ASIC 70 sends to the switch control circuit 81 a signal which instructs execution of the switch control for the active mode. In accordance with this instruction, the switch control circuit 81 executes the switch control for the active mode shown in FIG. 3, to thereby turn the switches SW1, SW4, SW7 and SW8 off, and to turn the switches SW2, SW3, SW5 and SW6 on. As shown in FIG. 2, the constant current Icp is continuously supplied to the Vs cell 38 of the gas detection element 30, the operational amplifier OP1 and the PID control circuit 71 are connected to the Ip+ port and the Pout port, and the pump current Ip is supplied to the Ip cell 37. As described above, the voltage generated across the detection resistor Rd, through which the pump current Ip flows, is detected by the first differential amplification circuit 73, and is sent, as the output (detection signal) of the full-range air-fuel-ratio sensor 10, from the Vout port to the microcomputer 60 via the A/D converter 98.

As shown in FIG. 4, in the microcomputer 60 of the ECU 100, the CPU 61 operates as follows. After the ASIC 70 has entered the active mode (S9: NO, S23: YES), the CPU 61 obtains the detection signal of the full-range air-fuel-ratio sensor 10 (S31), and detects the oxygen concentration (gas concentration) of the exhaust gas by applying a known computation, and finally detects the air-fuel ratio of the exhaust gas (S33). The detected air-fuel ratio of the exhaust gas is used for control of other circuits (devices) connected to the ECU 100, for example, control of injection timing of fuel, etc. After that, the CPU 61 proceeds to S35 so as to wait an elapsed time of 10 msec, and then returns to S5 so as to repeat S5 to S35.

Figure 2:
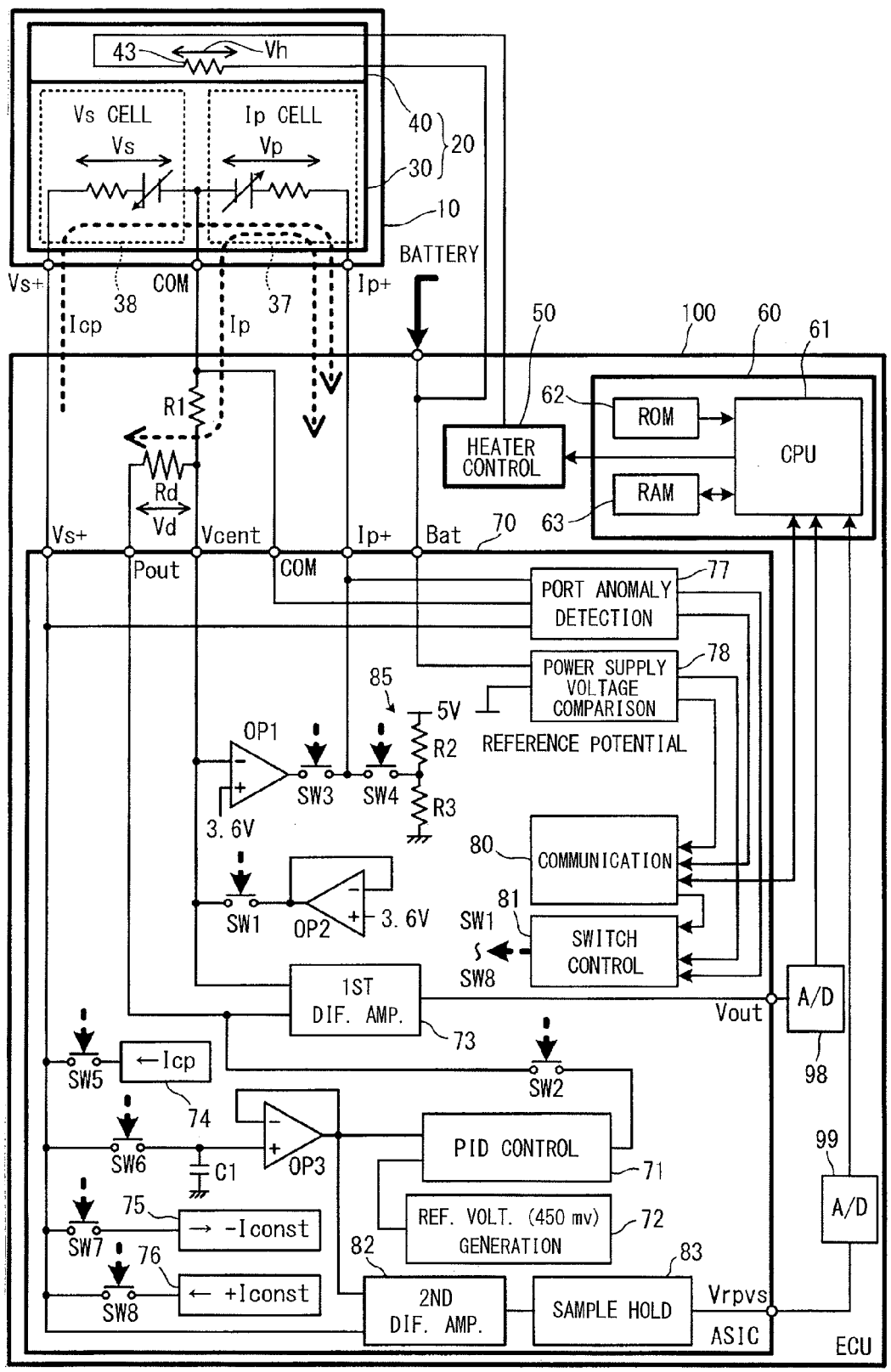
FIG. 2 is a diagram showing the electrical configuration of an ASIC.

Irrespective of the energization mode, a case may arise where, while S5 to S35 are repeatedly executed, the port anomaly detection circuit 77 of the ASIC 70 shown in FIG. 2 detects an anomaly, such as a short circuit, wire breakage, or the like, on the basis of the potentials of the Vs+ port, the COM port and the Ip+ port. In this case, the port anomaly detection circuit 77 sends to the switch control circuit 81 a signal which instructs execution of the switch control for the protection mode. In accordance with this instruction, the switch control circuit 81 turns all the switches SW1 to SW8 off, and forcedly switches the energization mode to the protection mode, to thereby stop the supply of electric current to the gas detection element 30. Furthermore, the port anomaly detection circuit 77 writes in the transmission buffer of the communication circuit 80 a report signal (flag) which reports that the ASIC 70 has entered the protection mode.

As a result, the report signal which reports the occurrence of a port anomaly is sent to the microcomputer 60. In the case where a report signal regarding the port anomaly is sent in the non-active mode or the active mode, not in the protection mode, in which case the port anomaly is ignored, when the microcomputer 60 receives the report signal (S7: YES), the CPU 61 proceeds, via S15 to S17 described below, to S19 so as to switch the energization mode to the protection mode. This is because the present energization mode is not the protection mode (S14: NO). That is, the CPU 61 stores an instruction signal in the transmission buffer in order to instruct the ASIC 70 to enter the protection mode. Also, the CPU 61 changes the value of the mode flag so as to indicate that the present energization mode is the protection mode. Moreover, the CPU 61 resets the counter (timer counter) (S21), whereby an elapsed time of 500 msec, which is the condition for bringing the ASIC 70 into the non-active mode, starts again. Subsequently, the CPU 61 proceeds to S35.

The ASIC 70 has already entered the protection mode in accordance with the instruction from the port anomaly detection circuit 77. Thus, the energization mode for the full-range air-fuel-ratio sensor 10 grasped by the microcomputer 60 coincides with the state of control of the switches performed in the ASIC 70, and the drive of the gas detection element 30 is started from the initial state.

Furthermore, in the case where the battery voltage monitored by the power-supply-voltage comparison circuit 78 becomes lower than the reference potential as well, the switch control circuit 81 executes the switch control for the protection mode. That is, all the switches SW1 to SW8 are turned off, whereby the energization mode is forcedly switched to the protection mode, and the supply of electric current to the gas detection element 30 is stopped. In addition, a report signal is written in the transmission buffer of the communication circuit 80.

In the case where a port anomaly (a short circuit or wire breakage) is detected when the ASIC 70 is in the non-active mode or in the active mode and the ASIC 70 enters the protection mode in S19, conventionally, the microcomputer 60 determines that an anomaly has occurred, and performs, for example, a process of turning a sensor anomaly lamp on, while maintaining the protection mode.

However, even in the case where a port anomaly is detected, in some cases, the detection is erroneous (wiring is normal) or the port anomaly is a temporary wiring anomaly which disappears immediately. If operation of the sensor is stopped every time such an anomaly is detected, the time required to return the sensor to the operation for gas concentration measurement is lost.

In order to solve this drawback, in the present embodiment, the processing of S15 to S17 is provided so as to determine that an anomaly has occurred only when the CPU 61 receives the report signal a plurality of times in S7.

Specifically, when the result of the determination in S14 is NO, the CPU 61 of the microcomputer 60 increments the anomaly determination counter n (S15), and then determines whether or not the value of n is equal to or greater than 3 (S16). When the result of the determination in S16 is YES, the CPU 61 of the microcomputer 60 first determines that an anomaly has occurred (S17), and then proceeds to S19. When the CPU 61 of the microcomputer 60 determines that an anomaly has occurred, for example, the CPU 61 performs, for example, a process of turning the sensor anomaly lamp on.

Meanwhile, the result of the determination in S16 is NO, the CPU 61 proceeds to S19 without determining that an anomaly has occurred. Subsequently, the CPU 61 proceeds to S13 via S21, S35, S5, etc., which have already described. In S13, the CPU 61 brings the ASIC 70 into the non-active mode. Subsequently, the CPU 61 returns to S7. When the result of the determination in S7 is YES and the result of the determination in S14 is NO, the CPU 61 increments the anomaly determination counter n in S15 as in the above-described case. As described above, in the present embodiment, the CPU 61 performs anomaly determination processing in S17 only when, after receiving a report signal in S7, the CPU 61 repeats a process a plurality of times in which the CPU 61 switches the energization mode to the protection mode in S19 and then to the non-active mode in S13, and receives the report signal again in S7 (a process from S13 to YES of S7).

As described above, according to the sensor control apparatus 100 of the embodiment of the present invention, when an anomaly (port anomaly or power supply voltage anomaly) of the state of electrical connection between the sensor control apparatus 100 and the sensor is detected in the drive mode (the non-active mode or the active mode) and the energization mode is switched to the protection mode, the energization mode is returned to the drive mode once, and the anomaly is first determined to have occurred when the anomaly is detected again after that. Therefore, when a wiring anomaly is erroneously detected or when a wiring anomaly or a like anomaly has occurred and disappears suddenly, such an anomaly is not determined to have actually occurred. Therefore, time is not lost in returning the sensor (the full-range air-fuel-ratio sensor 10) to the operation for gas concentration measurement.

Furthermore, in the case where energization mode has been returned to the drive mode once and an anomaly is detected again after that, the anomaly can be reliably determined to have occurred.

The present invention is not limited to the above-described embodiment, and various modifications may be made within the spirit and scope of the claims appended hereto. For example, the full-range air-fuel-ratio sensor 10 of the present embodiment is a two-cell-type gas sensor which includes the Ip cell 37, which serves as an oxygen pump cell, and the Vs cell 38, which serves as an oxygen concentration detection cell. However, the present invention may be applied to other types of gas sensors (e.g., a single-cell-type oxygen sensor, a three-cell-type $NO_X$ sensor, etc.).

In the present embodiment, the ASIC 70 is built in the ECU 100. However, a sensor drive circuit may be provided separately from the ECU 100. This also applies to the heater drive circuit 50. The heater drive circuit 50 may be built in the ECU 100, or may be provided separately as a heater control apparatus.

In the embodiment, the report signal output from the ASIC 70 is transmitted to the microcomputer 60 when clock synchronization communication is first performed between the ASIC 70 and the microcomputer 60 after the ASIC 70 detects an anomaly of its operation environment and performs the switch control for the protection mode. However, the timing of transmission of the report signal is not limited to the time when synchronization communication is first performed after the anomaly detection. The ASIC 70 may output the report signal when any of successive synchronization communications is established, so long as the report signal is output after the ASIC 70 is forced to enter the protection mode. Alternatively, the ASIC 70 may output the report signal not only at the time when synchronization communication is first performed after the anomaly detection, but also at a plurality of successive or intermittent times of establishing synchronization communication. Of course, the means for transmitting the report signal is not limited to clock synchronization communication. The ASIC 70 may have a dedicated or common port for reporting to the microcomputer 60 that the ASIC 70 has entered the protection mode.

This application is based on Japanese Patent Application No. 2010-29635 filed Feb. 15, 2010, incorporated herein by reference in its entirety.

What is claimed is:

1. A sensor control apparatus comprising:
    a signal output section which has a plurality of energization modes for a sensor that is to be connected to the sensor control apparatus, the energization modes including at least a drive mode for supplying electric current to the sensor and a protection mode for stopping the supply of electric current to the sensor to thereby protect the sensor, and which outputs an instruction signal for selecting one of the plurality of energization modes; and
    a sensor drive circuit for connection to the sensor and which enters one of the plurality of energization modes when the sensor drive circuit receives the instruction signal from the signal output section, so as to control the supply of electric current to the sensor, wherein
    the sensor drive circuit comprises:
    detection means for detecting, in the drive mode, an anomaly of the state of electrical connection between the sensor drive circuit and the sensor, protection means, operable when the detection means detects an anomaly of the connection state, for forcing the sensor drive circuit to enter the protection mode irrespective of the energization mode in which the sensor drive circuit has operated, and report means for reporting to the signal output section that the sensor drive circuit is in the protection mode, after the sensor drive circuit is forced to enter the protection mode by the protection means, wherein the signal output section comprises:

return means, operable when a report signal outputted by the report means is input to the signal output section, for outputting an instruction signal which instructs the sensor drive circuit to enter the protection mode, and then outputting an instruction signal which instructs the sensor drive circuit to enter the drive mode, and anomaly determination means for determining that an anomaly of the connection state has occurred, if the report signal is again input a predetermined number of times after the sensor drive circuit has entered the drive mode in response to the corresponding instruction signal output from the return means.

2. The sensor control apparatus according to claim 1, wherein the anomaly determination means determines that the anomaly of the connection state has occurred, when a phenomenon, in which the report signal is input again after the sensor drive circuit has entered the drive mode in response to the corresponding instruction signal output from the return means, occurs repeatedly a predetermined number of times which is set two or more times.

* * * * *